(12) United States Patent
Voute et al.

(10) Patent No.: US 8,177,123 B2
(45) Date of Patent: May 15, 2012

(54) SYSTEMS AND METHODS FOR FREEZING, STORING AND THAWING BIOPHARMACEUTICAL MATERIALS

(75) Inventors: Nicolas Voute, Chemin Peygros (FR); Jonathan Cutting, Fairfield, CA (US); Isabelle Gay, Peypin (FR)

(73) Assignee: Sartorius Stedim North America Inc., Bohemia, NY (US)

( * ) Notice: Subject to any disclaimer, the term of this patent is extended or adjusted under 35 U.S.C. 154(b) by 903 days.

(21) Appl. No.: 12/236,933

(22) Filed: Sep. 24, 2008

(65) Prior Publication Data
US 2010/0072216 A1    Mar. 25, 2010

(51) Int. Cl.
| | |
|---|---|
| G06F 17/00 | (2006.01) |
| F25C 1/00 | (2006.01) |
| B65D 21/02 | (2006.01) |
| B65D 25/20 | (2006.01) |
| B65B 5/00 | (2006.01) |

(52) U.S. Cl. ............. 235/375; 220/737; 220/23.83; 220/23.86; 220/592.13; 220/723; 220/495.05; 220/495.06; 220/4.07; 206/505; 206/508; 206/511; 206/524.1; 62/62; 62/66; 62/457.1; 53/473

(58) Field of Classification Search ............ 235/375; 220/23.83, 23.86–23.87, 23.89, 4.07, 495.05–495.06, 220/592.13, 723, 737; 206/505, 508, 511, 206/524.1; 53/473; 62/62, 66, 457.1
See application file for complete search history.

(56) References Cited

U.S. PATENT DOCUMENTS
| | | | |
|---|---|---|---|
| 2,633,006 | A | 3/1953 | Taylor |
| 2,722,111 | A | 11/1955 | Taylor |

(Continued)

FOREIGN PATENT DOCUMENTS
DE    3142521    11/1987

(Continued)

OTHER PUBLICATIONS

PCT/ISA/220—Notification of Transmittal of the International Search Report and the Written Opinion of the International Search Authority, dated Apr. 26, 2010, for corresponding International Application No. PCT/US2009/057241, filed on Sep. 17, 2009.

(Continued)

*Primary Examiner* — Michael G Lee
*Assistant Examiner* — Laura Gudorf
(74) *Attorney, Agent, or Firm* — Heslin Rothenberg Farley & Mesiti PC; Nicholas Mesiti, Esq.; Victor A. Cardona, Esq.

(57) ABSTRACT

A system for use in storing biopharmaceutical materials includes a holder and a container for holding biopharmaceutical materials therein. The container includes a storage portion and a sampling portion connected to each other by a connecting portion. The holder has a storage cavity receiving the storage portion and a sampling cavity receiving the sampling portion. The holder includes a first portion and second portion. The container is received between the first portion and the second portion to connect the container to the holder. The holder includes an interior storage cradle bounding the storage cavity of the holder. The holder includes an interior sampling cradle bounding the sampling cavity. The sampling cradle is separated from the storage cradle and connected to the storage cradle by a passage receiving the connecting portion connecting the storage portion to the sampling portion. An outer rim of the holder is connected to the cradle and separated from the cavity.

23 Claims, 4 Drawing Sheets

U.S. PATENT DOCUMENTS

| | | |
|---|---|---|
| 2,794,570 A | 6/1957 | Downs |
| 3,133,677 A | 5/1964 | Bertels |
| 3,244,311 A | 4/1966 | Lawson |
| 3,265,254 A | 8/1966 | Carter et al. |
| 3,586,097 A | 6/1971 | Bender et al. |
| 3,875,754 A | 4/1975 | Faust et al. |
| 3,986,506 A | 10/1976 | Garber et al. |
| 4,018,911 A | 4/1977 | Lionetti et al. |
| 4,211,267 A | 7/1980 | Skovgaard |
| 4,251,995 A | 2/1981 | Pert et al. |
| 4,315,409 A | 2/1982 | Prentice et al. |
| 4,317,665 A | 3/1982 | Prentice |
| 4,327,799 A | 5/1982 | Scheiwe et al. |
| 4,365,629 A | 12/1982 | Pert et al. |
| 4,460,365 A | 7/1984 | Ganshirt et al. |
| 4,474,016 A | 10/1984 | Winchell |
| 4,482,585 A | 11/1984 | Ohodaira et al. |
| 4,565,073 A | 1/1986 | Lavender |
| 4,783,042 A | 11/1988 | Folkmar |
| 4,811,465 A | 3/1989 | Folkmar |
| 4,869,398 A | 9/1989 | Colvin et al. |
| 4,993,579 A | 2/1991 | Burchett |
| 4,994,021 A | 2/1991 | Smith et al. |
| 5,168,725 A | 12/1992 | Margolin |
| 5,181,394 A | 1/1993 | Schea, III et al. |
| 5,197,601 A | 3/1993 | Sterett |
| 5,249,684 A | 10/1993 | Sterett |
| 5,250,044 A | 10/1993 | Irr et al. |
| 5,309,723 A | 5/1994 | Thomas et al. |
| 5,332,114 A | 7/1994 | Sano et al. |
| 5,361,906 A | 11/1994 | Sterett |
| 5,364,385 A | 11/1994 | Harms et al. |
| 5,431,496 A | 7/1995 | Balteau et al. |
| 5,435,142 A | 7/1995 | Silber |
| 5,465,865 A | 11/1995 | Coombes |
| 5,507,904 A | 4/1996 | Fisher et al. |
| 5,560,403 A | 10/1996 | Balteau et al. |
| 5,564,279 A | 10/1996 | Thomas et al. |
| 5,613,622 A | 3/1997 | Surrena et al. |
| D385,943 S | 11/1997 | Voelker |
| 5,756,193 A | 5/1998 | Yamamoto et al. |
| 5,863,715 A | 1/1999 | Rajotte et al. |
| 5,935,848 A | 8/1999 | Sputtek et al. |
| 5,988,422 A | 11/1999 | Vallot |
| 6,076,457 A | 6/2000 | Vallot |
| 6,146,124 A | 11/2000 | Coelho et al. |
| 6,186,932 B1 | 2/2001 | Vallot |
| 6,232,115 B1 | 5/2001 | Coelho et al. |
| 6,298,991 B1 | 10/2001 | Tsai |
| 6,302,327 B1 | 10/2001 | Coelho et al. |
| 6,371,643 B2 | 4/2002 | Saad et al. |
| 6,453,683 B1 | 9/2002 | Wisniewski et al. |
| 6,517,526 B1 | 2/2003 | Tamari |
| 6,550,966 B1 | 4/2003 | Saad et al. |
| 6,631,616 B2 | 10/2003 | Wisniewski et al. |
| 6,635,414 B2 | 10/2003 | Wisniewski |
| 6,648,143 B2 | 11/2003 | Robertson |
| 6,659,132 B2 | 12/2003 | Smith et al. |
| 6,670,175 B2 | 12/2003 | Wang et al. |
| 6,684,646 B2 | 2/2004 | Voute et al. |
| 6,698,213 B2 | 3/2004 | Voute et al. |
| 6,729,369 B2 | 5/2004 | Neas et al. |
| 6,764,482 B2 | 7/2004 | Keilman et al. |
| 6,769,231 B2 | 8/2004 | Danby |
| 6,786,054 B2 | 9/2004 | Voute et al. |
| 6,808,675 B1 | 10/2004 | Coelho et al. |
| 6,945,056 B2 | 9/2005 | Brown et al. |
| 6,996,995 B2 | 2/2006 | Voute et al. |
| 7,137,261 B2 | 11/2006 | Brown et al. |
| 7,225,949 B2 | 6/2007 | Kubo et al. |
| 2001/0043763 A1 | 11/2001 | Saad et al. |
| 2002/0121527 A1 | 9/2002 | Good |
| 2003/0017066 A1 | 1/2003 | Danby et al. |
| 2003/0198406 A1 | 10/2003 | Bibbo et al. |
| 2004/0031273 A1 | 2/2004 | Lanctot |
| 2004/0096126 A1 | 5/2004 | Danby et al. |
| 2004/0107150 A1 | 6/2004 | Neas et al. |
| 2004/0144799 A1 | 7/2004 | Danby et al. |
| 2004/0144800 A1 | 7/2004 | Danby et al. |
| 2004/0221897 A1 | 11/2004 | Schubmehl et al. |
| 2004/0254560 A1 | 12/2004 | Coelho et al. |
| 2005/0183976 A1 | 8/2005 | Brothers |
| 2006/0112717 A1 | 6/2006 | Walton |
| 2007/0084222 A1 | 4/2007 | Voute et al. |
| 2007/0125098 A1 | 6/2007 | Voute et al. |
| 2007/0209960 A1 | 9/2007 | Leoncavallo et al. |

FOREIGN PATENT DOCUMENTS

| | | |
|---|---|---|
| DE | 4308383 A1 | 3/1993 |
| DE | 29703691 U1 | 3/1997 |
| EP | 0521132 B1 | 5/1996 |
| EP | 1683506 A1 | 7/2006 |
| FR | 2449429 | 2/1980 |
| GB | 2046081 A | 2/1979 |
| JP | 54111998 | 9/1979 |
| JP | 2001149444 A | 6/2001 |
| JP | 2003205016 | 7/2003 |
| JP | 2005193013 | 7/2005 |
| WO | WO 9009184 | 1/1990 |
| WO | WO 9623703 | 8/1996 |
| WO | WO 02092462 | 11/2002 |
| WO | WO 2007104047 A2 | 9/2007 |

OTHER PUBLICATIONS

PCT/ISA/237—Written Opinion, dated Apr. 23, 2010, for corresponding International Application No. PCT/US2009/057241, filed on Sep. 17, 2009.

PCT/ISA/210—International Search Report, dated Apr. 23, 2010, for corresponding International Application No. PCT/US2009/057241, filed on Sep. 17, 2009.

SYSTEMS AND METHODS FOR FREEZING, STORING AND THAWING BIOPHARMACEUTICAL MATERIALS

TECHNICAL FIELD

This invention relates, in general, to biopharmaceutical materials, preservation methods and systems, and more particularly to systems and methods for freezing, storing and thawing biopharmaceutical materials.

BACKGROUND ART

Preservation of biopharmaceutical materials, such as cryopreservation, is important in the manufacture, use, transport, storage and sale of such materials. For example, biopharmaceutical materials are often preserved by freezing between processing steps and during storage. Similarly, biopharmaceutical materials are often frozen and thawed as part of the development process to enhance the quality or to simplify the development process.

When freezing biopharmaceutical materials, the overall quality, and in particular pharmaceutical activity, of the biopharmaceutical materials is desirably preserved, without substantial degradation of the biopharmaceutical materials.

The preservation of biopharmaceutical material, particularly in bulk quantities, often involves placing a container containing liquid biopharmaceutical material in a cabinet freezer, chest freezer or walk-in freezer and allowing the biopharmaceutical material to freeze. Specifically, the container, which is typically one or more liters in volume and may range up to ten or more liters, is often placed on a shelf in the cabinet freezer, chest freezer or walk-in freezer and the biopharmaceutical material is allowed to freeze. These containers may be stainless-steel vessels, plastic bottles or carboys, or plastic bags. They are typically filled with a specified volume to allow for freezing and expansion and then transferred into the freezers at temperatures typically ranging from negative 20 degrees Celsius to negative 70 degrees Celsius or below.

Disposable bulk storage containers such as plastic bags or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic bags, during freezing, thawing, or transportation of these containers often result in damage thereof, due, for example, to shock, abrasion, impact, or other mishandling events arising from operator errors or inadequate protection of the bags in use.

Similarly, thawing of bulk biopharmaceutical materials may involve removing them from a freezer and allowing them to thaw at room temperature. In certain situations thawing can also lead to product loss. In addition, in certain situations rapid thawing of biopharmaceutical materials may result in less product loss than slower thawing. Further, it may also be desirable to control temperature of the biopharmaceutical materials during a thawing process since exposure of some biopharmaceutical materials to elevated temperatures in certain situations may also lead to product loss. For example, it may be desirable to maintain a thawing biopharmaceutical material at about 0° C. when still in liquid and solid form during thawing thereof. In situations where thawing is desirable it is necessary to protect the biopharmaceutical material from damage which may occur due to impact or rupture to the containers.

Also, in certain situations it is desirable to analyze the quality or other characteristic(s) of biopharmaceutical materials held in a container. It is necessary to thaw an entire quantity of biopharmaceutical material frozen in such a container while analysis results are only required for a small portion of the total volume in the container.

Thus, there is a need for systems and methods for freezing, thawing, and storing biopharmaceutical materials, including containers and holders for such containers usable for the freezing, thawing, transporting and storing of biopharmaceutical materials. Also, there is a need for systems and methods which allow the testing of a portion of a processed biopharmaceutical material without thawing and testing an entire quantity of such processed biopharmaceutical materials.

SUMMARY OF THE INVENTION

The present invention provides, in a first aspect, a system for use in freezing, storing and thawing biopharmaceutical materials which includes a holder and a container for holding biopharmaceutical materials therein. The container includes a storage portion and a sampling portion connected to each other by a connecting portion. The holder has a storage cavity receiving the storage portion and a sampling cavity receiving the sampling portion. The holder includes a first portion and second portion. The container is received between the first portion and the second portion to connect the container to the holder. The holder includes an interior storage cradle bounding the storage cavity of the holder. The holder includes an interior sampling cradle bounding the sampling cavity. The sampling cradle is separated from the storage cradle and connected to the storage cradle by a passage receiving the connecting portion connecting the storage portion to the sampling portion. An outer rim is connected to the cradle and separated from the cavity.

The present invention provides, in a second aspect, a system for use in freezing, storing and thawing biopharmaceutical materials which includes a container for holding biopharmaceutical materials therein. A sensor is coupled to the container for monitoring a physical parameter of the biopharmaceutical materials in the container. A holder has a storage cavity receiving the container and a sampling cavity receiving the sensor. The holder includes a first portion and a second portion. The container is received between the first portion and the second portion to connect the container to the holder. The holder includes an interior storage cradle bounding the storage cavity. The holder includes an interior sampling cradle bounding the sampling cavity. The sampling cradle is separated from the storage cradle and connected to the storage cradle by a passage of the holder. The holder includes an outer rim connected to the storage cradle and separated from the storage cavity.

The present invention provides, in a third aspect, a method for use in freezing, storing or thawing biopharmaceutical materials which includes receiving a container holding biopharmaceutical materials in a holder having a storage cavity and a sampling cavity. The container is connected to the holder by receiving the container between a first portion and the second portion of the holder. An interior storage cradle of the holder bounds the storage cavity. An interior sample cradle of the holder bounds the sampling cavity. The sampling cradle is separated from the storage cavity. The sample cavity is connected to the storage cavity by a connecting passage of the holder. An outer rim of the holder is connected to the storage cradle and separated from the storage cavity.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION

In accordance with the principles of the present invention, systems and methods for freezing, thawing and storing biopharmaceutical materials are provided.

In an exemplary embodiment depicted in FIGS. 1-4, a system 5 for cooling, freezing, preserving, processing and thawing biopharmaceutical materials is shown. The system may include a sterile container, such as a flexible container 10, configured to contain the biopharmaceutical materials and configured to be supported by a supporting and/or protective structure, such as a holder 15.

Figure 1:
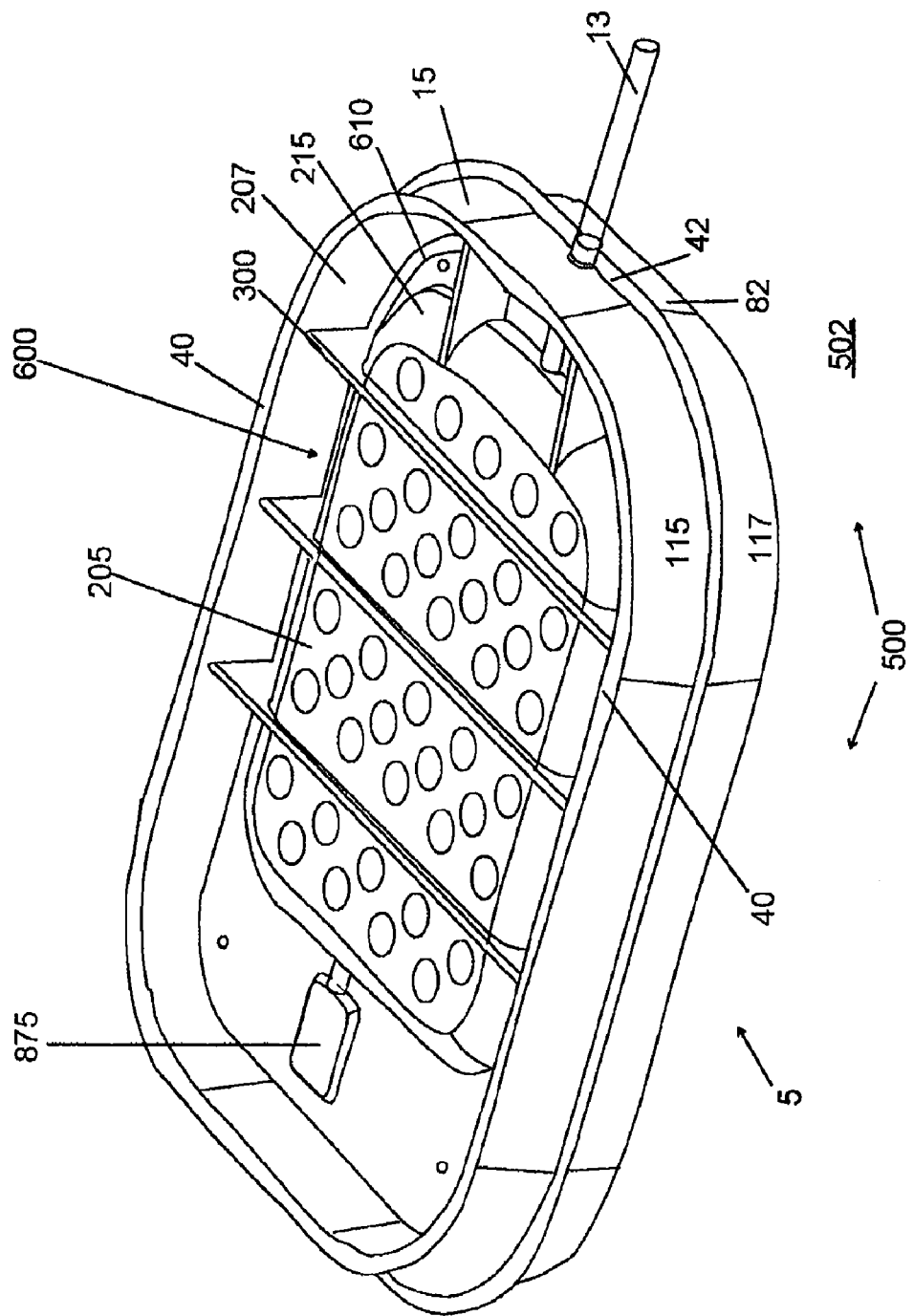
FIG. 1 is a perspective view of a holder receiving a container in accordance with the present invention.
Figure 2:
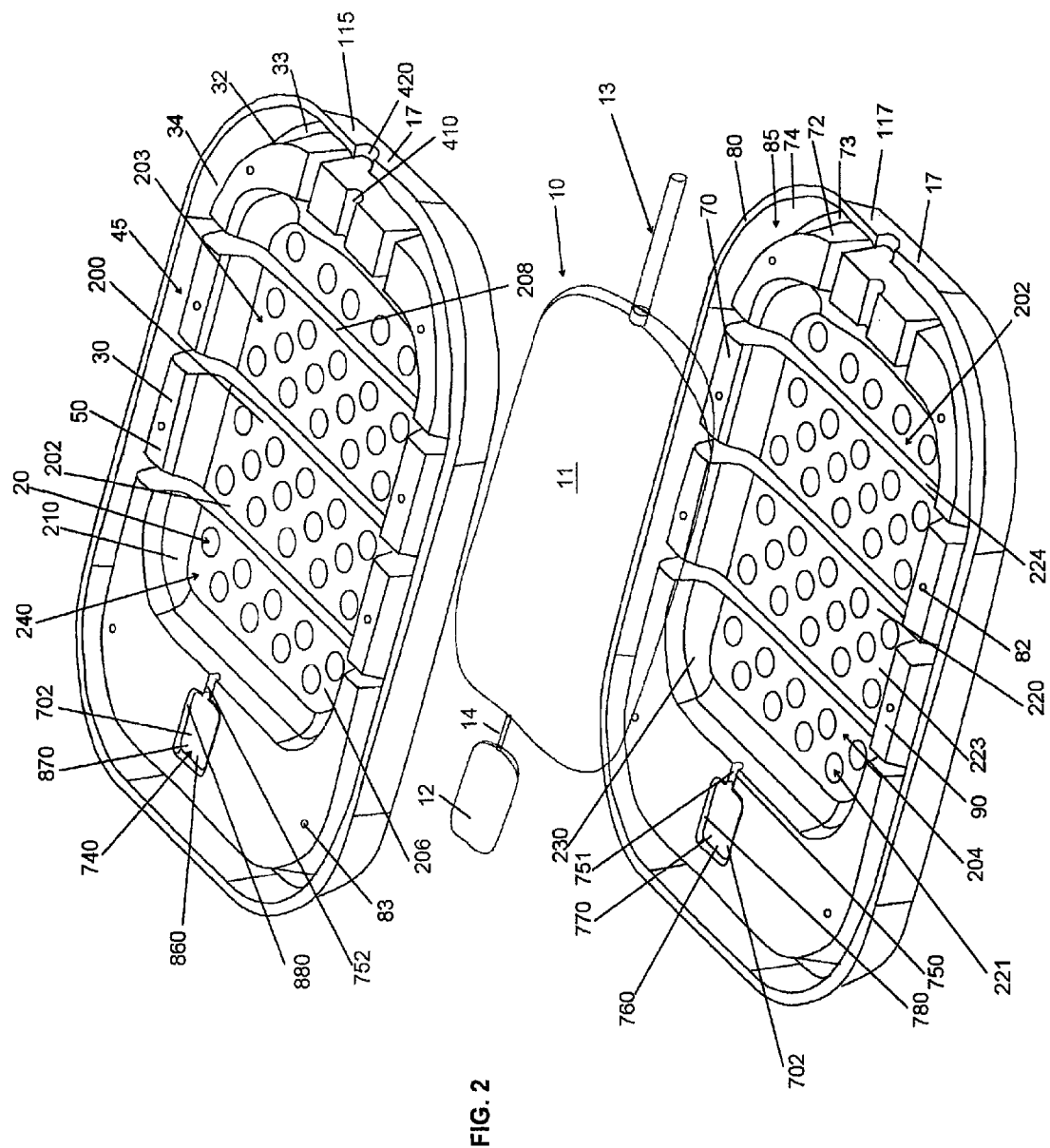
FIG. 2 is an exploded perspective view of a first portion and second portion of the holder of FIG. 1 showing a container therebetween not depicted in FIG. 1.

Flexible container 10 may be formed of a laminated film which includes a plurality of layers and may have an interior volume ranging from 0.01-100 liters, (e.g., 0.1-20 L) as depicted in FIG. 2 for example. Further, flexible container 10 could be available in a variety of sizes to accommodate different uses, for example, 5-10 liter flexible containers, such as 8-liter containers, may be utilized. Also a biocompatible product-contacting layer of the interior of flexible container 10 may be formed of a low density polyethylene, very low density polyethylene, ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with warm and cold conditions and may be able to withstand ionizing and gamma irradiation for sterilization purposes. Also, flexible container 10 may have a large surface area to volume ratio, and a relatively thin wall thus promoting heat transfer therethrough when received in a temperature control unit such as an interior 500 of a walk-in or blast freezer (FIG. 1). One example of materials useful for formulation of flexible container 10 is described in U.S. Pat. No. 5,988,422 to Vallot, the entire subject matter of which is hereby incorporated herein by reference.

Container 10 may be adapted to receive and contain frozen and/or liquid biopharmaceutical materials. In an embodiment, the biopharmaceutical materials may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, antibodies and their fragments, enzymes and their fragments, vaccines, viruses and their fragments, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, mixtures of the above and biocatalysts and their fragments.

Container 10 may be configured (e.g., shaped and dimensioned) to be received in, and connected to holder 15, which acts as a protector, supporting structure or frame for supporting flexible container 10, as depicted in FIGS. 1-2. In one example, container 10 may have a pillow-shape. Holder 15 may be configured to protect a container held therein during filling, transport, storage, and/or freezing of biopharmaceutical materials. For example, holder 15 may hold and protect container 10 during freezing of biopharmaceutical materials in interior 500 of a walk-in or blast freezer (FIG. 1). Further, holder 15 may protect container 10 when holder 15 is stacked on or under another holder similar to holder 15.

For example, holder 15 may include a first holder portion 115 and a second holder portion 117 forming a storage cradle 202 having a storage cavity 240 when connected to one another. First portion 115 has a first storage portion 203 having a bottom 200 and upwardly curving sides 210. Second portion 117 has a second storage portion 204 having a bottom 220 and upwardly curving sides 230. Bottom 200, upwardly curving sides 210, bottom 220 and upwardly curving sides 230 form storage cradle 202 which bounds storage cavity 240.

First portion 115 and second portion 117 may also form a sample cradle 702 having a sample cavity 740 when connected to one another. Sample cavity 740 may be connected to storage cavity 240 via a connecting portion 750 defined by a first half 751 and a second half 752, which may form a cylinder, for example, when first portion 115 and second portion 117 are connected to each other.

First portion 115 has a first sample portion 860 having a bottom 870 and upwardly curving sides 880. Second portion 117 has a second sample portion 760 having a bottom 770 and upwardly curving sides 780. Bottom 770, upwardly curving sides 780, bottom 870 and upwardly curving sides 880 form sample cradle 702 which bounds sample cavity 740.

Container 10 may include a storage portion 11 and a sample portion 12 connected by a connecting portion 14 which may be substantially cylindrical. Storage portion 11 may be received in storage cavity 240 and sample portion 12 may be received in sample cavity 740 while connecting portion 14 is received in connecting portion 750. Storage portion 11, sample portion 12 and/or connecting portion 14 may be connected to first holder portion 115 and/or second holder portion 117. For example, container 10 may be heat sealed or otherwise connected to first portion 115 and/or second portion 117 to prevent or inhibit separation of container 10 therefrom.

Storage portion 11, sample portion 12 and/or connecting portion 14 may be filled with biopharmaceutical materials. Storage portion 11 and sample portion 12 may be sealed relative to one another (e.g., in a portion of connecting portion 14) after such filling such that sample portion 12 may be disconnected from storage portion 12 and removed from holder 15 to allow the biopharmaceutical materials held in sample portion 12 to be tested, analyzed or otherwise processed while biopharmaceutical materials remain sealed in storage portion 11 in holder 15. The separation of storage portion 11 and sample portion 12 therefore allows analysis of the biopharmaceutical materials in the sample portion without requiring that the storage portion be opened, thawed or otherwise disturbed. Such separate analysis of the smaller amount of biopharmaceutical materials in the sample portion allows one to be reassured of the quality or other characteristic of the biopharmaceutical materials held in the storage portion without requiring the disturbance of the seal for such storage portion. Because the biopharmaceutical materials were originally inserted into both the sample and storage portions at the same time and the handling (e.g., exposure thereof to freezing, processing and/or other environmental factors) within holder 15 are substantially the same, one can be assured that the quality and other characteristics within the sample portion and the storage portion are substantially the same.

An inner rim 30 of first portion 115 may be connected to an outer rim 40 of first portion 115 as depicted in FIG. 2. Inner rim 30 may include a substantially flat holding or clamping portion 50 which may extend partially or entirely around an inner circumference of holder 15. Similarly, an inner rim 70 of second portion 117 may be connected to an outer rim 80. Inner rim 70 may include a substantially flat holding or clamping portion 90 which may extend partially or entirely around an inner circumference of holder 15. The holding or clamping portions may also include a plurality of openings spaced around a circumference thereof. These openings may receive pins to connect first portion 115 to second portion 117. For example, first portion 115 may receive pins (not shown) in openings 83 which may then be received in openings 82 of second portion 117 when the first and second portions are connected to each other. In another example, first portion 115 and second portion 117 could include connecting portions such as those described (e.g., teeth 350) in co-owned U.S. application Ser. No. 11/963,106 which is hereby incorporated herein by reference.

Holding or clamping portion 50 and holding or clamping portion 90 may be configured to hold or clamp container 10 therebetween before it is filled with biopharmaceutical materials to center the container in cradle 202 and cavity 240. For example, holding portion 50 and holding portion 90 may be spaced from each other to provide a particular amount of friction to container 10 such that as container 10 is filled with the biopharmaceutical materials, an edge or portion of the container may move from a position between the holding portions, or external to the holding portions, into cavity 240. Thus, as container 10 is filled with biopharmaceutical materials, container 10 may expand in storage cradle 202 to conform to the inner surfaces (i.e., bottom 200, upwardly curving sides 210, bottom 220 and upwardly curving sides 230) of storage cradle 202 bounding storage cavity 240 and the inner surfaces (e.g., bottom 770, upwardly curving sides 780, bottom 870 and upwardly curving sides 880) of sample cradle 702 bounding sample cavity 740.

A protective cavity 45 of holder 15 may be bounded by outer rim 40 which is connected to inner rim 30 as depicted in FIGS. 1-2. Also, a protective cavity 85 of second portion 117 may be bounded by outer rim 80 which is connected to inner rim 70. Protective cavity 45 and protective cavity 85 may extend circumferentially around holder 15. Outer rim 40 may include an inner wall 32 adjacent inner rim 30, a bottom surface 33 and an outer wall 34. Outer rim 80 may include an inner wall 72 adjacent inner rim 70, a bottom surface 73 and an outer wall 74. The protective cavities (i.e., cavity 45 and cavity 85) allow holder 15 to receive stresses, impacts, or shocks to an outer wall 17 of holder 15 while inhibiting or preventing damage to container 10 held in cavity 240. For example, an impact to outer wall 17 may cause outer wall 17 to temporarily move towards the inner rims into the protective cavities such that the outer walls of the outer rims absorb or dampen the shock and damage to the container is inhibited. Outer wall 17 may include outer wall 34 forming an exterior surface of outer rim 40 of first portion 115 and outer wall 74 forming an exterior surface of outer rim 80 of second portion 117. Outer wall 17 may be formed of elastically deformable or resilient materials such as PET or HDPE. Further, each of first portion 115 and second portion 117 may be formed monolithically or they may be formed of separate elements connected together. Also, protective cavities 45 and 85 may provides storage for conduits including tubing, connectors and clamps therefor.

Bottom 200 and bottom 220 may include a plurality of first openings 201 and a plurality of second openings 221, which may allow heat transfer from an exterior of holder 15 to biopharmaceutical materials held in container 10 in cavity 240 of holder 15. Any number of apertures and any design or placement of the apertures relative to one another on the bottoms may be provided to facilitate such heat transfer while still allowing the bottoms to provide structure/support to a container in cradle 202. Further, the openings may be placed relative to one another and the container may be formed of material such that the container remains offset from the openings (i.e., toward an interior of the cradle) when the biopharmaceutical materials held therein are in a liquid form. The offset of the container's surface from the openings inhibits any potential damage to the container from external hazards which may come near bottom 200 or bottom 220. Bottom 770 and 780 could also include such openings to facilitate heat transfer.

Also, bottom 200, bottom 220, sides 210 and sides 230 of cradle 202 may be connected to outer rim 40 by one or more support members or support ribs 300 providing structural support as depicted in FIG. 1, for example. Such ribs may extend across bottom 200 to connect bottom 200 and opposite sides of outer rim 40 to one another. Also, the ribs may extend across bottom 220 to connect opposite sides of outer rim 80 to one another and to bottom 220. Alternatively, one or more of ribs 300 may extend from outer rim 40 to bottom 200 or sides 210 without extending from one side of outer rim 40 to another side thereof. Ribs 300 may be raised relative to an exterior surface 205 of bottom 200 and an external surface 875 of bottom 870 as depicted in FIG. 1. An interior side 206 of bottom 200 may also include grooves 208 (FIG. 2) which correspond to ribs 300 on exterior surface 205 of bottom 200. Similarly, ribs 300 may be connected to bottom 220 and sides 230 and/or to opposite sides of outer rim 80 to provide structural support to cradle 202. Also, ribs 300 may be raised relative to an exterior surface (not shown) of bottom 220 while an interior surface 223 may have grooves 224. Ribs 300 may also be raised relative to an exterior surface 775 of bottom 770. The connection of support ribs (e.g., ribs 300) to cradle 202 structurally supports the cradle and inhibits deformation of a shape of the cradle in response to expansion of biopharmaceutical materials held in container 10 due to freezing. In another example, holder 15 may not have ribs 300 and instead may be reinforced by rods or cushioned by pads formed of textiles, foam, or other resilient materials.

As indicated above, the container (e.g., container 10) may avoid extending into openings 201 and 221 (or other openings if present in cradle 702) when biopharmaceutical materials held in the container are in a liquid form. Further, the container may also avoid extending into grooves 208 when such biopharmaceutical materials are in a liquid form. Upon the biopharmaceutical materials undergoing a freezing process, the container and biopharmaceutical materials held therein may extend into grooves 208, openings 201, and openings 221. The movement of freezing biopharmaceutical materials into grooves 208, openings 201, and openings 221 provide locations for expansion of the biopharmaceutical materials thereby allowing for less expansion of bottom 200 and bottom 220 in directions away from one another than would otherwise be the case absent the movement of biopharmaceutical materials into these locations.

Further, a space 600 may extend between exterior surface 205 of bottom 200 and an exterior surface 207 of inner wall 32 of outer rim 40 as depicted in FIG. 1. Space 600 may also be bounded by an exterior surface 215 of upwardly extending sides 210 and a bottom 610 of space 600, which may be an exterior surface of corresponding clamping portion 50 and connecting surface 90 on the opposite side of holder 15. As described above relative to protective cavity 45 and protective cavity 85, the space between outer rim 40 and exterior surface 205 of bottom 200 may provide protection to container 10 held in cradle 202. In particular, an impact, shock or stress to outer rim 40 may cause outer rim 40 (e.g., exterior surface 207) to move into, or deform (e.g., elastically or resiliently) toward space 600 thereby absorbing the impact, shock or stress and inhibiting the impact, shock or stress from being applied to container 10 and the biopharmaceutical materials held therein. Similarly, a space (not shown) may be provided between an exterior surface (not shown) of bottom 220 and outer rim 80 to inhibit damage to container 10 and biopharmaceutical materials held therein.

Outer rim 40 may have a height different than exterior surface 205 of bottom 200 and an external surface 875 of bottom 870 and ribs 300 thereon such that outer rim 40 is raised relative to exterior surface 205, exterior surface 875 and ribs 300 as depicted in FIG. 1. The difference in height between the outer rim and the exterior surfaces of the bottoms of the holder allows expansion of biopharmaceutical materials held in container 10 in cradle 202 due to freezing while avoiding the exterior side (i.e., exterior surface 205 and exterior surface 875) extending beyond outer rim 40. Similarly, outer rim 80 may have a height different than the exterior surface (not shown) of bottom 220, bottom 770 and ribs 300 thereon such that outer rim 80 is raised relative to the exterior surface and ribs 300 thereby allowing expansion of biopharmaceutical materials held in container 10 in cradle 202 due to freezing while avoiding the exterior side of bottom 220 from extending beyond outer rim 80.

Further, water and aqueous solutions expand by about ten percent when frozen and such expansion may be non-uniform. In one example, when container 10 is received in cradle 202 and cradle 702 the container may be filled with biopharmaceuticals such that cradle 202 and cradle 702 may accommodate the expansion due to freezing of the biopharmaceutical materials, i.e., the cradles are not filled with biopharmaceutical materials to their volumetric capacity in a liquid state and instead space exists to allow expansion of the biopharmaceutical materials within cradle 202 and cradle 702.

Further, the difference in height between each of the outer rims and the exterior surfaces of the bottoms of the holder (i.e., even after freezing of the biopharmaceutical materials) inhibits damage to the biopharmaceutical materials held in container 10, along with container 10 itself. In particular, the bottoms (e.g., bottoms 200, 770, 870 and 220) of the holder are recessed relative to the outer rim(s) and therefore may not contact any objects adjacent to holder 15 or abutting holder 15 resulting from such objects instead contacting the outer rim(s), as depicted in FIG. 5. For example, when holder 15 lies horizontally on a surface 502 of interior 500 of a blast freezer, outer rim 80 may contact the surface and outer rim 40 may contact an object (e.g., a second holder) stacked on top of holder 15, but neither bottom 200 nor bottom 220 may contact the surface or the object due to the space between the exterior surface (e.g., exterior surface 205 and exterior surface 875) of the bottoms and any object resulting from the difference in height between the outer rims and the exterior surfaces of the bottoms.

The outer rims (e.g., outer rim 40 and outer rim 80) may also have teeth to allow holder 15 to be connected (i.e., by interlocking the teeth) to a second similar holder having complementary teeth on an outer rim thereof as shown relative to holder 15 and 515, for example, in FIGS. 1 and 5 of co-owned application Ser. No. 11/963,106. The difference in height between the outer rims and exterior surfaces also allows the stacking of multiple holders (e.g., multiple holders 15) on the outer rims thereof and the engagement of the corresponding teeth in contrast to stacking the exterior surfaces (e.g., exterior surface 205) on each other. For example, the difference in heights between the outer rims and exterior surfaces is advantageous particularly when such exterior surfaces (e.g., exterior surface 205 and exterior surface 875) may be deformed (e.g., by a mounding effect) due to the expansion of freezing biopharmaceutical materials held in containers therein thereby making stacking difficult. In this case, the stacking of the holders on the outer rims minimizes any interference that may be caused by deformation of the exterior surfaces. More particularly, the height difference between the rims and the exterior surfaces allow the expansion of the biopharmaceutical materials held in container 10 in cradle 202 toward an outer surface of the outer rim (e.g., outer rims 40 and 80) while avoiding the exterior surfaces from extending beyond the outer surfaces of the outer rims. The expansion of the exterior surface beyond the outer rims may otherwise (i.e., absent the raised height of the rims relative to the exterior surfaces) inhibit the stacking of another holder on top of holder 15 due to the uneven surfaces provided by the expansion of the biopharmaceuticals held in container 10.

Outer rim 40 may include a bottom end 42 and outer rim 80 may include a top end 82, which may be connected to one another via heat sealing, or some other means of fixedly and/or sealingly connecting the outer rims to one another as depicted in FIG. 1. For example, flanges (not shown) may also be provided which extend outwardly from outer rims 40 and 80 to allow first portion 115 and second portion 117 to be mechanically fastened to each other using fasteners, such as pop rivets, ratcheting fasteners, other fasteners, screws or bolts. Also, such connection may be done by welding (e.g., heat sealing, high frequency sealing or ultra sonic welding) or with adhesive. Such a connection may inhibit contamination from passing by outer rim 40 and outer rim 80 toward container 10.

The outer rims (e.g., outer rim 40 and outer rim 80) and the inner rims (e.g., inner rim 30 and inner rim 70) may include apertures such as a first aperture 420 and a second aperture 410 depicted in FIG. 2. to allow conduits (e.g., a conduit 13) connected to container 10 to pass therethrough. Such conduits may allow filling or draining of biopharmaceutical materials or other solids, liquids, or gases into and/or out of the interior (not shown) of container 10. Conduit 13 may also be used to insert a measurement probe (not shown) inside container 10 (e.g., a pH electrode, a conductivity sensor, temperature probe, an ion selective electrode, a spectrophotometric probe, an ultrasound sensor, an optic fiber.)

Conduit 13 may be integral (e.g., monolithic relative) to container 10 or it may be connectable to a receiving port (not shown) thereof. For example, conduit 13 could be connected to a receiving port using a fitting placed within the inlet port. Fittings such as those described in U.S. Pat. No. 6,186,932, may be used for the connection of such conduits. Also, fittings which can maintain the sterility of the contents of the container or flexible container may preferably be used. The fittings may be configured in different shapes, such as straight fittings and/or angled fittings including ninety (90) degree elbows, if desired. In another example, conduit 13 may include a filter (not shown) to filter any impurities or other undesirable materials from the biopharmaceutical material. The conduit and/or fittings may be located in protective cavity 45 and/or protective cavity 85, which may protect conduit 13 and the fittings from any damage resulting from impact or stress, such as the impact resulting from a person dropping holder 15 when container 10 is filled with biopharmaceutical materials.

Figure 3:
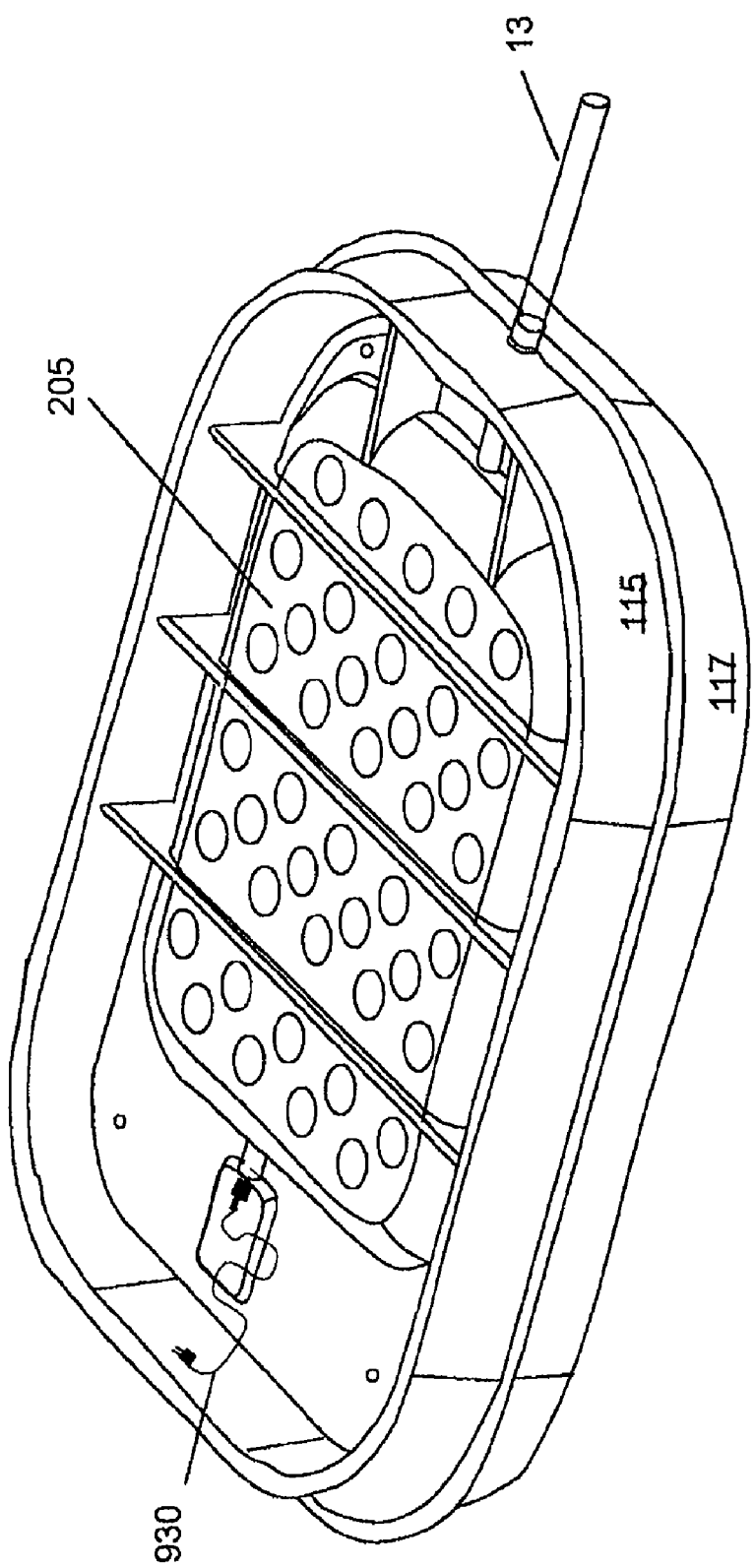
FIG. 3 is a perspective view of the holder of FIG. 1 receiving a monitoring device in accordance with the present invention.
Figure 4:
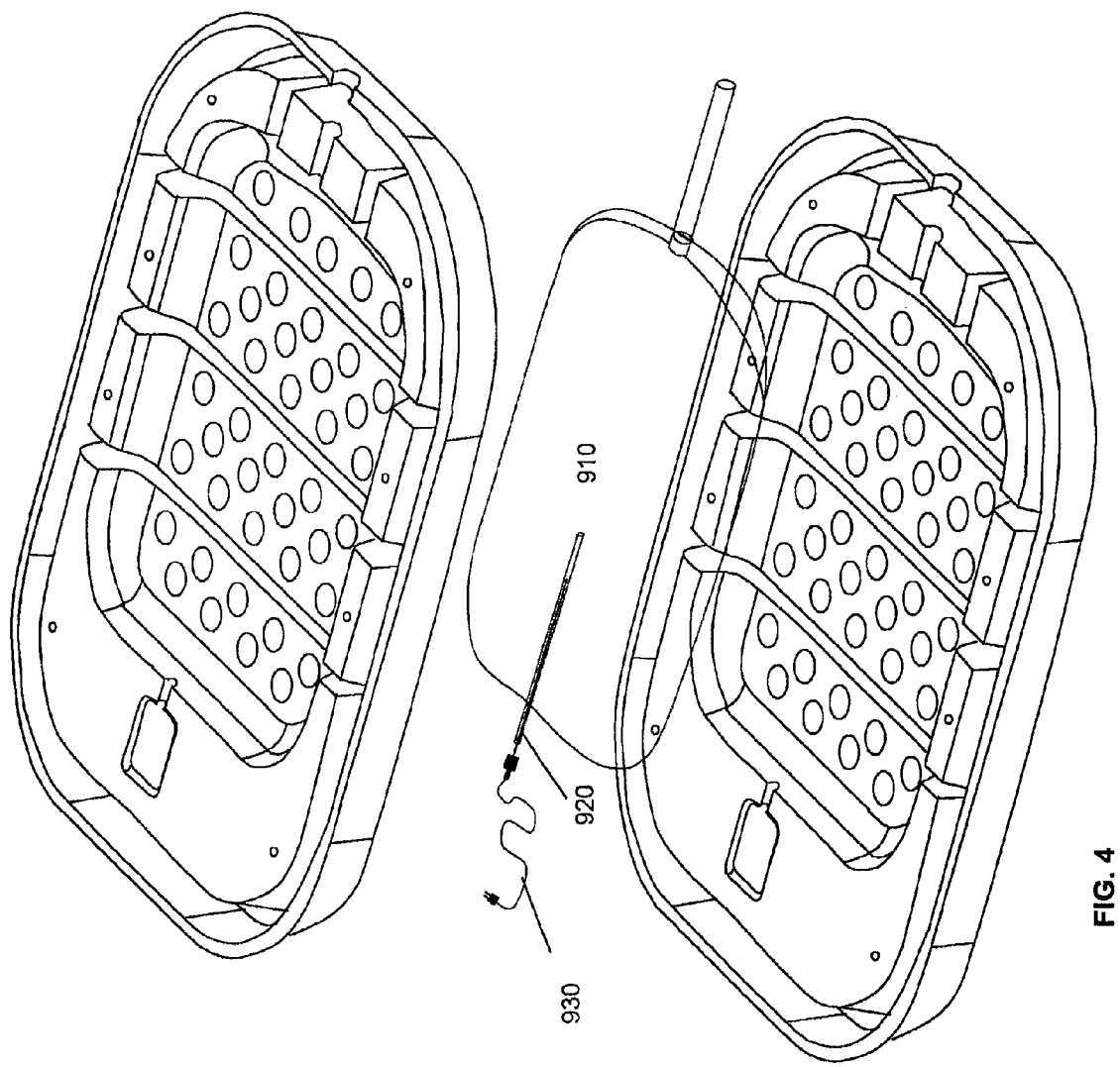
FIG. 4 is an exploded perspective view of the holder of FIG. 3 showing top and bottom portions thereof, and a container having a monitoring device therebetween.

In another example depicted in FIGS. 3-4, holder 15 receives a second container 910 having a monitoring device 920 (e.g., (e.g., a pH electrode, a conductivity sensor, temperature probe, an ion selective electrode, a spectrophotometric probe, an ultrasound sensor, an optic fiber) extending from an interior of container 910 through connecting portion 750 to sample cavity 740 where said monitoring device 920 may couple to a connecting cable 930 or other means of coupling the monitoring device to a computing unit or controller for processing data received from the monitoring device. The monitoring device may also include data logging and wireless communication (e.g., RFID) capability. For example, an identification signal may be transferred into a RFID tag at a product filling step. Such signal may be utilized to track the product during storage and distribution phases. The monitoring device (e.g., monitoring device 920) may record the physical parameters of the biopharmaceutical materials during the processing thereof and such data may be communicated to a computing unit at the conclusion of the processing via the coupling of the data logging system to a computing logging system or via wireless transmission during the processing thereof.

Also, the holders (e.g., holder 15) described above may preferably be formed of materials configured to support a weight of container 10 and to protect container 10 from being punctured or damaged due to an impact or stress on holder 15. For example, holder 15 may be more rigid than container 10 held therein. Also, the materials forming holder 15 may remain stable and retain their structural properties over a large range of temperatures. Specifically, such materials should retain their load-bearing capacity and exhibit cold crack temperatures no higher than negative 80 degrees Celsius while being resistant to cleaning agents and methods commonly used in biopharmaceutical manufacturing, e.g., sodium hydroxide, sodium hypochloride (e.g., CLOROX), peracetic acid, etc. For example, first portion 115 and second portion 117 of holder 15 could be formed of injection molded plastic or thermo formed plastic, such as PET (e.g., Clear 0.05" PET) or HDPE (e.g., 0.080" black unfilled HDPE). Also, holder 15 may be formed of fluoropolymer resin (e.g. TEFLON), machined plastic, stainless steel or any number of other materials including aluminum, polyethylene, polypropylene, polycarbonate, and polysulfone, for example. Further materials may include composite materials such as glass-reinforced plastic, carbon-fiber reinforced resins, or other engineering plastic materials known to offer high strength-to-weight ratios and which are serviceable at various temperatures of interest. In one example, an exterior part of the holder may be formed of a rigid or semi-rigid material while in the inner part of the holder in contact with the container may be formed of a softer material such as a foam or an elastic material. The softer material will allow expansion of the liquid biopharmaceutical material during freezing. It will be understood by those skilled in the art that each of first portion 115 and second portion 117 may be monolithic and formed as one piece or may include elements fixedly connected together. In addition, portions 115 and 117 may be constructed as one piece such that the portions 115, 117 may be hinged or otherwise connected together. Further, holder 15 could be formed of a single material (e.g., injection molded plastic) or it could be formed of different materials and connected together. Also, holder 15 may be formed of a material resistant to sterilization by gamma radiation.

Also, a holder (e.g., holder 15) and cradles (e.g., storage cradle 202 and sample cradle 702) thereof may be formed, sized and/or dimensioned to receive and support containers of various sizes to provide additional rigidity and support to the container(s), thus facilitating handling, storage, and/or temperature control thereof. For example, container 10 may be pillow shaped and holder 15 may be elliptically shaped.

Also, it will be understood by one skilled in the art that various holders (e.g., holder 15) may have cradles (e.g., cradle 202, cradle 702) configured (e.g., shaped and dimensioned) to receive various sized containers (e.g., container 10) and to be received in a temperature control unit (e.g., a blast freezer). Although the containers are described herein as flexible containers, the containers may be made of a semi-rigid material such as polyethylene or the like. An example of such a container could include a container similar to a standard plastic milk jug. Containers made of such similar semi-rigid materials may benefit from additional rigidity supplied by attachment (e.g., fixedly or releasably) to a holder, for example. Further, the containers whether formed of a rigid, flexible or semi-rigid material, contain outer surfaces which may contact the interior surfaces of a holder which may include holes and/or may be formed of a material to facilitate heat transfer to and from a container (e.g., container 10) held in such a holder (e.g., holder 15) when the holder is present in a temperature control unit, such as a blast freezer. Further, the outer surfaces of the holder receiving the containers for holding the biopharmaceutical materials may be in contact with air flow in an interior (e.g., interior 500) of a blast freezer or other means of temperature control to cause the cooling and/or heating of the container having the biopharmaceutical materials therein to cause the temperature of the biopharmaceutical materials to be controlled.

In another example, holder 15 may be formed of a foam (e.g., HDPE, EVA), or a more rigid material (e.g., foam or solid) may be utilized with such a foam to form the holder. Also, a container, such as container 10, may be connected to a holder, such as holder 15, by RF welding or mechanical attachment. In a further example, a container and holder may be separated from one another within cradle 202 and/or cradle 702 by a layer of collapsible dimples (not shown) or ribs (not shown). Also, holders (such as holder 15), may include a first portion (e.g., first portion 115) and a second portion (e.g., second portion 117) which are connected to each other by hinges to allow the interior (e.g., storage cradle 202 and sample cradle 702) to be accessed while the first and second portions remain connected to one another.

The biopharmaceutical material in the containers (i.e., container 10) and holders (e.g., holder 15) described above may thus be cooled or otherwise thermoregulated (e.g., to a sub-zero temperature) in a temperature control unit, such as a blast freezer providing forced convection, for example. Alternatively, the biopharmaceutical materials may be frozen in a conventional laboratory freezer providing free convention, a plate freezer or via a liquid nitrogen path. When such freezing operation is completed, the containers may be removed from the temperature control unit by removing the containers and the holders, or other support structures which the containers are received in or connected to, for example. The holders or other support structures holding the containers may be stored in a large chiller or freezer with an interior air temperature of about negative 20 degrees Celsius, for example.

A typical process for processing and/or preserving a biopharmaceutical material is described as follows. One or more containers (e.g., container 10) is received in and/or connected to a holder (e.g., holders 15) as depicted in FIGS. 1-4. Also, holder 15 may be aligned substantially horizontally (e.g., such that outer rim 40 or outer rim 80 is flat on a surface) and biopharmaceutical material, for example liquid biopharmaceutical material, may be inserted through conduit 13 into container 10. Also, after biopharmaceutical material is received in the interior of the holder (e.g., holder 15) through a conduit (e.g., conduit 13), a sample portion (e.g., sample portion 12), and a storage portion (e.g., storage portion 11) may be sealed relative to one another (e.g., sealed in a portion of connecting portion 14). Holder 15 may then be located in a temperature control unit, such as an interior 500 of a blast freezer, as shown in FIG. 1. The biopharmaceutical contents may be frozen in the temperature control to negative 20 degrees Celsius or below, for example. After the biopharmaceutical material in the container(s) is frozen, holder 15 and the container(s) may be stored in the temperature control unit, such as a blast freezer, or removed therefrom and placed in a large freezer, for example, a walk-in freezer having an interior air temperature of about negative 20 degrees Celsius for storage, as is typically present in large medical institutions (e.g., hospitals). Also, the use of containers (e.g., container 10) having a uniform thickness allow uniform cooling to occur within such a temperature control unit, blast freezer, or other means for controlling a temperature of the immediate surroundings of such containers. Further, the contents of sample portion 12 may be removed from the remainder of container 10 at any time to allow the analysis of sample portion 12 which would provide an indication of the characteristics of both the sample portion and the storage portion, since they would both be filled with the same material and exposed to the same environmental conditions.

Also, container 910 may be utilized with holder 15 and the contents of container 910 may be monitored throughout the processing described above via monitoring device 920 which could be a temperature sensor, pH sensor or sensor for monitoring any characteristic of the biopharmaceutical materials held therein. Such monitoring may be stored on a storage medium (e.g., a computer disk, processor, flash drive, etc) and which may later be transferred to a computing unit for analysis. Alternatively, the monitoring device may be coupled to a computing unit during the processing steps, (e.g., via a computer cable or wirelessly).

Further, the above-described containers may be removed from a freezer or other system for storage of the flexible containers and contents thereof at a controlled temperature. These containers having biopharmaceutical material therein may then be received in a temperature control unit for heating, melting, agitating, mixing and/or thawing the biopharmaceutical material contained in the containers. For example, holder 15 supporting container 10 having frozen biopharmaceutical material therein may be placed in a temperature control unit where its temperature may be controlled (e.g. thawed) by heat transfer plates or air convection (e.g., free or forced air) heating. Also, the biopharmaceutical materials may be thawed in a water bath or in air and ambient temperature. In addition, holder 15 may be submitted to gentle mixing inside a temperature control unit to accelerate the thawing kinetics and to minimize any solute concentration gradient in the thawed liquid.

As described above, a holder (e.g., holder 15) may include a storage portion and a sample portion. Such holders may also include multiple such sample portions to hold sample portion(s) of containers (e.g., sample portion 12) and/or monitoring device(s) (e.g., monitoring device 920). For example, a holder could include a first sample cradle holding a sample portion of a container and a second sample cradle holding a monitoring device or multiple such cradles holding a combination of sample portions and monitoring devices.

From the above description, it will be understood to one skilled in the art that the containers described herein may be adapted for use in holders of various shapes or sizes. Further, the holders may be adapted to receive containers of various shapes or sizes. These holders or support structures may be configured for long or short term storage of the containers containing biopharmaceutical materials in liquid or frozen state, or may be adapted to transport the flexible containers containing biopharmaceutical materials in liquid or frozen state. Further, these holders and containers may be adapted for utilization with materials other than biopharmaceutical materials.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A system for use in storing biopharmaceutical materials, said system comprising:
   a container for holding biopharmaceutical materials therein, said container comprising a storage portion and a sampling portion connected to each other by a connecting portion;
   a holder having a storage cavity receiving said storage portion and a sampling cavity receiving said sampling portion;
   said holder comprising a first portion and a second portion, said container received between said first portion and said second portion to connect said container to said holder;
   said holder comprising an interior storage cradle bounding said storage cavity;
   said holder comprising an interior sampling cradle bounding said sampling cavity, said sampling cradle separated from said storage cradle and connected to said storage cradle by a passage receiving the connecting portion connecting said storage portion to said sampling portion; and
   said holder comprising an outer rim connected to said storage cradle and separated from said storage cavity.

2. The system of claim 1 wherein an interior of said sampling portion is sealed from an interior of said storage portion to inhibit fluid communication between said sampling portion and said storage portion.

3. The system of claim 2 wherein said sampling portion is sealed from said storage portion at a location on the connecting portion.

4. The system of claim 1 wherein said storage cradle comprises a bottom and edges extending upwardly from said bottom.

5. The system of claim 4 wherein said bottom comprises an inner surface facing said cavity receiving said container and an outer surface, said outer surface of said bottom being recessed relative to an outer surface of said outer rim.

6. The system of claim 1 wherein said sampling cradle comprises a bottom and edges extending upwardly from said bottom.

7. The system of claim 6 wherein said bottom comprises an inner surface facing said cavity receiving said sampling portion of the container and an outer surface, said outer surface of said bottom being recessed relative to an outer surface of said outer rim.

8. The system of claim 1 wherein said holder comprises a sensor received in a third cavity and coupled to the container for monitoring a physical parameter of biopharmaceutical materials received in the container.

9. The system of claim 1 wherein said holder further comprises a second sampling cavity configured to receive at least one of a second sampling portion of the container and a monitoring device.

10. The system of claim 1 wherein said holder further comprises a second sampling cavity receiving a monitoring device coupled to the biopharmaceutical material received in at least one of the storage cavity and the sampling cavity.

11. A system for use in storing biopharmaceutical materials, said system comprising:
a container for holding biopharmaceutical materials therein,
a sensor coupled to said container for monitoring a physical parameter of the biopharmaceutical materials in the container;
a holder having a storage cavity receiving said container and a sampling cavity receiving said sensor;
said holder comprising a first portion and a second portion, said container received between said first portion and said second portion to connect said container to said holder;
said holder comprising an interior storage cradle bounding said storage cavity;
said holder comprising an interior sampling cradle bounding said sampling cavity, said sampling cradle separated from said storage cradle and connected to said storage cradle by a passage of said holder; and
said holder comprising an outer rim connected to said storage cradle and separated from said storage cavity.

12. The system of claim 11 wherein the sensor extends from the sampling cavity to contact the container.

13. The system of claim 11 further comprising a data storage device configured to store information regarding the monitoring the physical parameter.

14. The system of claim 11 wherein the data storage device comprises a controller.

15. The system of claim 11 wherein said holder comprises a third cavity separated from said container cavity and said sampling cavity, said third cavity comprising a tracking information signal generator for sending information regarding the physical parameter of the biopharmaceutical materials.

16. The system of claim 11 further comprising a tracking information signal generator for sending information regarding the physical parameter of the biopharmaceutical materials.

17. The system of claim 11 further comprising an RFID tag for sending information regarding the physical parameter of the biopharmaceutical materials.

18. The system of claim 11 wherein said storage cavity comprises a bottom having an inner surface facing said cavity receiving said container and an outer surface, said outer surface of said bottom being recessed relative to an outer surface of said outer rim.

19. The system of claim 11 wherein the physical parameter comprises a temperature of the biopharmaceutical materials in the container.

20. A method for use in storing biopharmaceutical materials, the method comprising:
receiving a container holding biopharmaceutical materials in a holder having a storage cavity and a sampling cavity;
connecting the container to the holder by receiving the container between a first portion and a second portion of the holder;
an interior storage cradle of the holder bounding the storage cavity;
an interior sampling cradle of the holder bounding the sampling cavity, the sampling cavity separated from the storage cavity, and the sampling cavity connected to the storage cavity by a connecting passage of the holder; and
an outer rim of the holder connecting to the storage cradle and separated from the storage cavity.

21. The method of claim 20 wherein a sampling portion of the container is connected to a storage portion of the container by a connecting portion of the container, the storage portion received in the storage cavity, the sampling portion received in the sampling cavity, and the connecting portion received in the connecting passage.

22. The method of claim 21 further comprising receiving a monitoring device in the sampling cavity and monitoring a characteristic of the biopharmaceutical materials by coupling the monitoring device to the biopharmaceutical materials.

23. A system for use in freezing, storing and thawing biopharmaceutical materials, said system comprising:
a container for holding biopharmaceutical materials therein, said container comprising a storage portion and a sampling portion connected to each other by a connecting portion;
a holder having a storage cavity receiving said storage portion and a sampling cavity receiving said sampling portion;
said holder comprising a first portion and a second portion, said container received between said first portion and said second portion to connect said container to said holder;
said holder comprising an interior storage cradle bounding said storage cavity;
said holder comprising an interior sampling cradle bounding said sampling cavity, said sampling cradle separated from said storage cradle and connected to said storage cradle by a passage receiving the connecting portion connecting said storage portion to said sampling portion;
said sampling portion separated from said storage portion at a sealed portion between said sampling portion and said storage portion; and
said holder comprising an outer rim connected to said storage cradle and separated from said storage cavity.

* * * * *